United States Patent [19]
Ahlqvist et al.

[11] Patent Number: 5,881,534
[45] Date of Patent: Mar. 16, 1999

[54] PROCESS FOR STERILIZATION BY RADIATION AND BY THE USE OF AN OXYGEN ABSORBER, A CONTAINER AND A MEDICAL ARTICLE STERILIZED BY THE PROCESS

[75] Inventors: Anna Ahlqvist, Stockholm; Kjell Berglund, Järfälla; Stefan Lundmark, Drottningholm, all of Sweden; Jimmie Ward, Letterkenny, Co., Ireland

[73] Assignee: Pharmacia & Upjohn AB, Stockholm, Sweden

[21] Appl. No.: 750,245

[22] PCT Filed: Jun. 8, 1995

[86] PCT No.: PCT/SE95/00684

§ 371 Date: Feb. 21, 1997

§ 102(e) Date: Feb. 21, 1997

[87] PCT Pub. No.: WO95/33651

PCT Pub. Date: Dec. 14, 1995

[30] Foreign Application Priority Data

Jun. 8, 1994 [SE] Sweden ................................ 9401986-6

[51] Int. Cl.$^6$ ........................... B65B 31/00; B65B 55/02; A61L 2/08
[52] U.S. Cl. ................ 53/403; 53/425; 53/432; 53/510; 422/22
[58] Field of Search ...................... 53/403, 432, 111 RC, 53/474, 425, 510; 206/205, 204; 422/22, 23, 28

[56] References Cited

U.S. PATENT DOCUMENTS

| | | |
|---|---|---|
| 4,192,773 | 3/1980 | Yoshikawa et al. ................... 206/205 |
| 4,899,517 | 2/1990 | Shima et al. .............................. 53/432 |
| 4,998,400 | 3/1991 | Suzuki et al. . |
| 5,014,494 | 5/1991 | George ...................................... 53/432 |
| 5,202,052 | 4/1993 | Zenner et al. . |
| 5,510,166 | 4/1996 | Inoue et al. .............................. 53/474 |
| 5,577,368 | 11/1996 | Hamilton et al. ........................ 53/432 |

FOREIGN PATENT DOCUMENTS

| | | |
|---|---|---|
| 0093796 | 11/1983 | European Pat. Off. . |
| 0218003 | 4/1987 | European Pat. Off. . |
| 0510687 | 10/1992 | European Pat. Off. . |
| 603789 | 6/1994 | European Pat. Off. . |
| 61104974 | 5/1986 | Japan . |
| 63152570 | 6/1988 | Japan . |
| 452710 | 12/1987 | Sweden . |
| 1230959 | 5/1971 | United Kingdom . |
| WO90/00907 | 2/1990 | WIPO . |

OTHER PUBLICATIONS

"Radiation Effects on Polymers Ed." by R.L. Cough, et al., ACS Symposium Series, 475, 1991.

"Stabilization of Polyolefins to Gamma Irradiation–Role of the Initial Radicals" by D.J. Carisson et al., ACS, 433, 1991.

*Primary Examiner*—James F. Coan
*Assistant Examiner*—Eugene L. Kim
*Attorney, Agent, or Firm*—Gilbert M. Villacorta, Ph.D, Pepper Hamilton LLP

[57] ABSTRACT

A novel process for sterilizing an article made from polymeric material by radiation sterilization. The article is enclosed in a gas impermeable package together with an oxygen absorber for a time sufficient to consume substantially all the oxygen in the package and the oxygen dissolved in the polymeric material. The article is prefereably intended for medical use and can contain a radiation sterilizable parenterally administerable preparation.

15 Claims, No Drawings

PROCESS FOR STERILIZATION BY RADIATION AND BY THE USE OF AN OXYGEN ABSORBER, A CONTAINER AND A MEDICAL ARTICLE STERILIZED BY THE PROCESS

FIELD OF INVENTION

The present invention is directed to a novel process for sterilizing an article made from polymeric materials by radiation sterilization. The article is enclosed in an gas impermeable package together with an oxygen absorber for a time sufficient to consume substantially all of the oxygen in the package and the oxygen dissolved in the polymeric material. The article is preferably intended for medical use and may contain a radiation sterilizable parenterally administerable preparation.

BACKGROUND OF THE INVENTION

Sterilizing medical articles of polymeric materials can be performed by a number of methods, such as steam sterilization (autoclavation), radiation sterilization (electron beam (EB), β- and γ-radiation), ethylene oxide (EtO) and aqueous formaldehyde. Each method has its specific advantages and disadvantages and will be selected with respect to the chemical structure of the polymeric material. If the material is employed as a packaging material, the selection also depends on the characteristics of the enclosed goods.

A technical problem that requires especially careful consideration is the sterile packaging and storing of parenterally administerable fluids that both are sensitive to atmospheric oxygen during storage and incompatible with many polymeric materials and their additives.

In known manufacturing technologies, the most rigorous methods involve filling a bag with the medical fluid in the presence of an inert gas, sealing the bag and subjecting it to steam sterilization and thereafter placing it, still in an oxygen free atmosphere, with an oxygen absorber in an outer oxygen impermeable envelope. Such a process, as for example described in the U.S. Pat. No. 4,998,400, is, however, both laborious and resource consuming.

Oxygen absorbers have previously been successfully used for the packaging of oxygen sensitive medical fluids like amino acid solutions and fat emulsions. The absorbers have been positioned between an inner medical container made from a gas pervious polymer material filled with the medical solution and an outer enclosing sheet made of an gas impermeable material. Such packages are disclosed by e.g. the European patent specifications EP-A-0 093 796 and EP-A-0 510 687.

Sterilization by irradiation is a desirable alternative method to heat sterilization, since it will provide a simpler and less costly manufacturing process. It is, however, a technique that must be carefully considered, because of the chemical and physical alterations that can be induced in the polymeric material in the presence of atmospheric oxygen.

EP-B-0 218 003 discloses a radiation sterilized medical device enclosed in a gas permeable bag which is irradiated with γ-radiation and thereafter placed in a gas impermeable wrapping member together with a deoxidizing agent. Both residual oxygen and ozone resulting from the gamma radiation will thereby be absorbed and because the entry of oxygen from the external environment is almost completely prevented, an oxygen-free condition within the wrapping is obtained. The purpose of the technique disclosed in EP 0 218 003 is primarily to prevent the "gamma"-odour associated with ozone.

The British patent specification 1,230,950 describes a similar method of sterilizing material packaged together with an oxygen scavenger with γ-radiation.

The sterilizing methods according to these patent specifications may, however, lead to the formation of undesired and potentially deleterious degradation products originating from free radicals of the polymeric material and the small amounts of dissolved oxygen that remains in the polymeric material during the γ-irradiation. The activity of the highly reactive free radical containing molecules may to a certain degree pervade the original polymeric structure of the material by bond cleavage and macroradical formation, thereby making the material discoloured or changing its mechanical properties.

In theory, a layered polymeric material with adhered or built-in oxygen scavengers, as disclosed in the Japanese patent applications JP 61104974 and JP 63152570, may at least partially the problems of secondary effects originating from dissolved residual oxygen in the material. In practice, the γ-radiation will cause local overheating in the material that leads to thermal oxidation that destroys the oxygen scavengers.

Much industrial effort has been devoted to the search for non-colouring radiation systems, especially for medical devices made of polypropen. The chemically aggressive radicals or products thereof may also damage sensible medical fluids stored in containers made of irradiated polymers. This tends to be especially disadvantageous when the fluids consist of sensitive amino acid solutions and/or lipid emulsions containing polyunsaturated fatty acids that are intended to be stored for a considerable time period.

The various methods for stabilizing polymers against such primary and secondary events of occurring in materials exposed to high-energy radiation include electron and ion scavenging, energy transfer processes, radical scavenging and acceleration of radical decay. Such methods are normally costly and do not always introduce processes and compounds that are compatible with sensible medical products. There is a very restricted knowledge of how such compounds may interfere with sensitive fluids during storage. Moreover, in the field of pharmaceuticals, there is a general desire from medical authorities that additives in any form shall be excluded from products on the market. Besides that, only a few additives have been found in practice to reduce the number of radicals generated in a polymer by a given γ-radiation dose. Most of these additives are unacceptable for use, especially for medical articles, because of their intense yellow discoloration. Some of them may possibly accelerate post-γ-degradation. Another approach has been to use an additive, not to prevent radical formation, but instead to speed the (hopefully harmless) decay of these radicals. This concept of radical "mobilization" has been clearly shown to speed radical decay, and to improve long-term stability in the case of polypropen. It has been shown that the decay of macroradicals formed from irradiation of polypropen under vacuum is accelerated by PE-waxes, atactic polypropen and hydrocarbon, in order of increasing effectiveness. None of these additives is, however, preventing the ion-electron reactions or deactivating excited states, as they are formed during the irradiation.

An important necessity for medical equipment to be γ-sterilized is the substantially complete absence of contamination. This effectively eliminates all colour-forming antioxidants such as phenols (yellow-brown products) or aromatic amines (red-brown products) from plastic medical articles, see D. J. Carlsson et al. in Radiation Effects on Polymers Ed. by R. L. Clough et al., ACS Symposium Series 475, 1991.

Hindered amines such as those based on 2,2,6,6,-tetramethylpiperidine operate as antioxidants at ambient temperatures in light-stabilization packages. Furthermore they and their products are colourless or only very weakly absorbing. These aliphatic amines have been previously shown to function as stabilizers to post-γ-irradiation oxidation of polyolefines, a phenomenon explained on page 433, Chapter 26 "Stabilization of polyolefines to Gamma Irradiation" in the above cited D. J. Carlsson et al.

The irradiated polyolefin will, due to the production of free radicals among other compounds form hydroperoxides, which may be decomposed under the formation of even more free radicals. Highly efficient stabilizer combinations might possibly suppress oxidation to the point where atypical hydroperoxide products dominate. Post-irradiation oxidation is largely dependent upon initiation by the slow thermal decomposition of the hydroperoxides. Hydroperoxide decomposition by an additive, such as hindered amines, will also prevent this oxidative degradation. However, in medical applications all such additives are generally avoided, since they tend to discolour the articles and may migrate from the material and consequently introduce a toxicity risk.

The following description, given in order to clarify, the primary and secondary events taking place in polymers during, and after radiation sterilization, is based on the teachings by D. J. Carlsson et al. in Radiation Effects on Polymers Ed. by R. L. Clough et al., ACS Symposium Series 475, 1991, which hereby is incorporated by reference.

The primary radiation process appearing from irradiation of polymers can produce a number of different reactions, such as crosslinking, backbone scission and hydrogen evolution. Various chemical products can result from the occurrence of the complex cascade of events such as reactions (1)–(6) below, which are typical of gamma-irradiation.

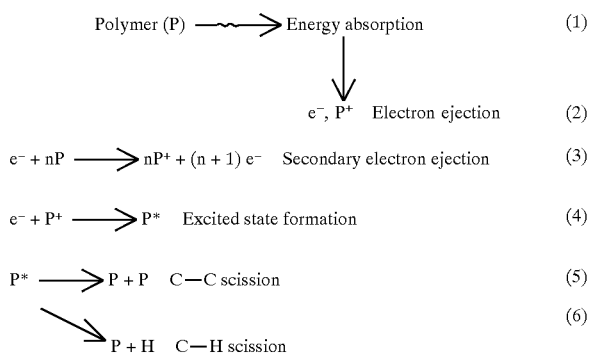

At room temperature, the ion-electron recombination occurs quickly enough to give highly excited states (P*) and cations. At low temperatures (<−100° C.), ejected electrons may be trapped in the polymer matrix. The excited states dissipate some of their excess energy by bond scission to give free radicals. The scission of C—H bonds is favoured over C—C backbone scission.

Secondary reactions in irradiated polymers appear when the free radicals produced in reactions (5) and (6), above, lead to the formation of chemical products, commonly associated with radiation effects. The combination of macroalkyl radicals or their addition to unsaturated sites leads to chain branching and/or crosslinking. Hydrogen atoms mainly abstract from the polymer chain to give molecular hydrogen and fresh macroalkyl radicals (reaction (7)).

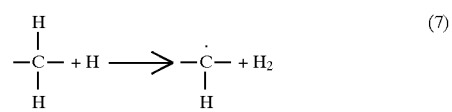

In some polymers, main chain scission is followed by monomer elimination. Macroradical combination results in crosslink formation (reaction (8)).

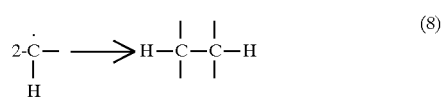

Unsaturation is a major product from irradiated polyolefins and is believed to result from migration of radical sites by an inter- and intra-molecular hydrogen atom transfer until two sites come together. Unsaturated products with conjugated double bonds resulting from radiation can have an undesired discoloured appearance.

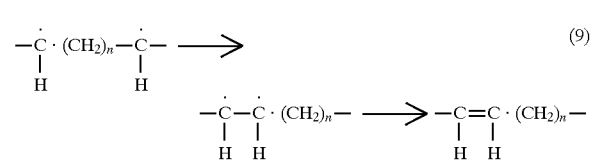

In the absence of oxygen, the net result of irradiation is the composite result of reactions (5)–(9) so that crosslinked gel or a degradation of molecular weight results. The behaviour of various polymers irradiated in the absence of oxygen may be generalized into those which crosslink during irradiation; polyethylene, poly(methyl acrylate), poly(acrylic acid), polystyrene) and those which degrade (poly(methyl methacrylate), poly(methacrylic acid), poly(α-methylstyrene), poly(butene-2). Polypropen undergoes both scission and crosslinking. Crosslinking increases the stiffness of plastics and can render them inextensible. Poly (olefin sulphones) have been shown to be exceptionally sensitive to γ- or electron-beam radiation and can be used as short-wavelength photoresists. Chain scission also leads to embrittlement, but the effect of direct, radiation-induced scission in commodity polymers is normally minor compared with oxidative chain scission.

Because of its biradical nature, $O_2$ reacts at close to the encounter frequency with carbon-centred radicals to give peroxyl radicals, by reaction (10). A relatively slow hydrogen abstraction from the polymer matrix by the peroxyl radicals, reaction (11), completes a cycle of reactions which cause the progressive oxidation of the polymer.

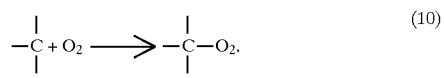

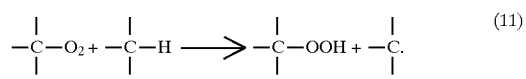

The first molecular product, the hydroperoxide group, is thermally unstable and cleaves readily at the O—O linkage to give a pair of radicals and so leads to a branching, thermal oxidation during storage after irradiation. This effect is of major concern when sterilizing medical equipment, implants, etc. by γ-radiation.

The loss of physical properties in many polymers containing aliphatic backbone substituents results from the β-scission of alkoxyl radicals, reaction (12). The alkoxyl radicals are formed by hydroperoxide decomposition.

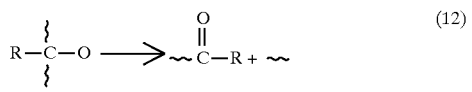

They are also formed in the complex self-reaction of peroxyl radicals which may terminate the radicals. Elongation at break has been shown to be appreciably more sensitive to degradation than tensile strength.

The radiation sensitivity of polymeric materials is generally affected by impurities, additives, dose rate, sample thickness and morphology. For example, the highly oriented, chain-extended morphology in highly drawn PE fibres is much more γ-irradiation-resistant than the usual melt-quenched semicrystalline morphology. This results both from restricted $O_2$ diffusion and effects on radical decay rates. It is therefore complicated to predict the marked effect of the dose rate.

It is the primary object of the present invention to reduce the secondary processes appearing in polymeric material during and after sterilizing dosages of γ-irradiation due to the presence of oxygen. It is of especial advantage to be able to eliminate the discolouring and the physical changes and degradation of polymeric materials that frequently appears after the use of conventional sterilization techniques.

A purpose with the present invention is also to obtain a safe and reproducible sterilization of sensitive medical objects without being dependent on expensive methods like evacuating air and introducing inert gases and steam sterilisation.

DESCRIPTION OF THE INVENTION

The invention is related to a process for sterilizing an article comprising a polymeric material by means of radiation, wherein the said polymeric material is enclosed in a gas impermeable package together with an oxygen scavenger containing a supply of water for a time sufficient to consume substantially all of the oxygen in the package, and also the oxygen dissolved in the matrix of the polymeric material. The package and its content is thereafter subjected to a sterilizing dosage of γ-radiation. In the process the article is preferably for medical use, but also other sensitive instruments and/or electronic articles are conceivable to sterilize, if they are compatible with γ-radiation.

In a special method the article to sterilize is a container made from a polymeric material filled with a radiation sterilizable product, wherein both the container and its content is subjected to the said process. The product is preferably a parenterally administerable medical preparation, but other products like nutrients are also possible to sterilize in this manner.

An important part of the present invention is the use of a water containing oxygen scavenger for removing substantially all oxygen dissolved in the matrix of a polymeric object that shall be subjected to sterilization by γ-radiation. A suitable oxygen scavenger, which is more detailly described below, is iron oxide based and contain crystalline water, but other deoxidizers are also conceivable.

Also parts of the present invention are a gamma-radiation sterilized medical article made of a polymeric material and a gamma-radiation sterilized container made of a polymeric material containing a radiation sterilizable medical product intended for parenteral administration, both produced by the mentioned process.

To successfully perform the inventive sterilization it is important that the polymeric material or the filled container made thereof is stored a predetermined suitable time period in a gas permeable enclosure or package together with the oxygen scavenger in order to consume substantially all oxygen, even the oxygen molecules dissolved in the polymeric matrix of the article. A suitable storage period of the article made of polymeric material together with the oxygen scavenger is from at least about 48 hours to several weeks. A number of factors will influence the length of the storage period, among which the most important is the chemical nature of the polymer and its affinity to the oxygen molecules, the capacity of the oxygen absorber, the number (or quantity) of absorbers and the volume enclosed by the gas impermeable package. However, it must to be regarded to be within the concept of the present invention to optimize this time period and the person skilled in the art shall have no difficulties to find out suitable storage conditions. Typical oxygen absorbers useful in the present invention will have a capacity of absorbing about 10 to 15 ml oxygen per hour. With the knowledge about the initial oxygen content of enclosed atmosphere, the kinetics of the absorber and the specific oxygen affinity of the polymeric material, an estimation of the storage time period to obtain substantially oxygen free conditions can be made for each system. It must also be considered to be within the inventive concept to find out suitable relations between storage time, characteristics and amount of the polymeric material and the amount and distribution of the oxygen scavenger present in the gas impermeable package. Suitable storage times to obtain substantially oxygen free conditions also within the matrix of the polymeric material will vary from about 48 hours to several weeks.

The said polymeric material can be a homogenous composition or be various mixtures including multilayered polymeric sheet materials. At least one polymer should belong to the category that can be secondarily oxidized and cross-linked as defined above.

The invention will be especially advantageous if the material includes polypropen and/or polyethylene, but anyone skilled in the art can find numerous alternatives.

The gas impermeable package preferably contains an aluminium layer or consists of an aluminium foil. Other examples of suitable materials are PVDC, EVOH, PVOH, plasma coated multilayered structures containing $SiO_x$, $Al_2O_3$ etc., certain aromatic nylons, such as MXD-6 and the multilayered structures in the international patent application PCT/SE94/00138.

The gas impermeable package containing the polymeric medical article or the polymeric container filled with a product for parenteral administration can optionally be sealed in an oxygen depleted atmosphere in the presence of nitrogen or another suitable inert gas. An important advantage of the invention is the possibility of sealing the gas impermeable package in air, without the use of inert gases, and still be able to obtain an advantageous γ-radiation sterilization without side reactions.

The container that is filled with a product for parenteral administration is preferably made of EVOH, polypropen, polyethylene, EVA, Excel®, Nylon-11 or other polymeric materials which are partially gas permeable. The filling and sealing procedure of the container is performed with conventional aseptic procedures and will not be further discussed herein.

The invention is applicable on a wide range of polymeric materials and parenterally administerable products. Especially preferred products are such intended for parenteral administration that must be stored after production and which contains high amounts of oxygen sensible and/or heat sensitive amino acids, proteins or lipid emulsions comprising sensitive unsaturated fatty acids. Such products can be stored either in fluid form or as dry powder in different compartments of a container together with an equally sterilized solvent that just before administration are reconstituted to a parenterally administerable liquid composition.

A suitable oxygen absorber is enclosed in a small bag and is used as a desiccant. Such oxygen absorbers are well known from the food industry and they are placed in a package of food to remove oxygen and prevent the food from deterioration due to the oxygen present. The food maintains its original taste, as there is no growth of mould and no progress of oxidation. There are basically two types of oxygen absorbers, those who demand the presence of water and those who contain bound (crystalline) water from the beginning. The latter type is preferably utilized in the present invention in combinations with a gas impermeable overwrap and a polymer material that is exposed to γ-irradiation. The former type can be used if water is supplied together with the oxygen absorber.

Oxygen absorbers composed of iron powder are especially preferred according to the present invention. They are based on the fact that rusting of iron requires oxygen. The oxidation mechanism is too complicated to be expressed by a single formula, but can generally be expressed as follows.

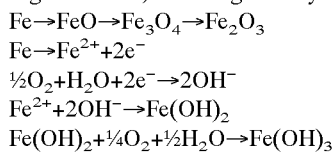

The doses of gamma-radiation used in the present invention are of a conventional magnitude with a dose rate of about 0.1 Mrad/hr and the irradiation doses of about 15 to 35 kGy.

In the following exemplifying part we have characterized irradiated materials by UV-, IR-spectroscopies, tensile strength (elongation at break), differential scanning calorimetry (DSC), thermal gravimetric analysis (TGA), chemiluminiscence, visual inspection and gas chromatographic/mass spectroscopic analysis of volatile by-products.

It is evident from the Examples 1.1 to 1.7 and Example 2 that polymeric articles sterilized by the method according to invention to a high degree maintain their original physical and mechanical properties and have reduced tendency to form potentially toxic by-products.

The following exemplifying part is not intended to delimit the scope of the present invention, as it is described by the appended claims, only to illustrate some easily reproducible selected tests.

Exemplifying Part of the Description

EXAMPLE 1

The investigated compound is a polypropen/Kraton mixture in a shape of 1 mm thick saddle-port system adjusted with an injection-port in natural rubber (latex). The trade name of the polypropen is Fina Dypro Z-7650, processed by Fina, and the trade name of the Kraton is Kraton G-1652, processed by Shell. The two materials are compounded by Ferro. An iron-based scavenger ZR-200, processed by Mitsubishi, is used when an oxygen free material shall be obtained and nitrogen when an oxygen free atmosphere shall be obtained.

Five polypropylene/Kraton saddles were overwrapped with an impermeable aluminium pouch (15 * 20 mm), which was covered with a polyethylene layer on the inside and a poly(ethylene terephtalate) layer on the outside. The samples were stored in the aluminium overwraps at an ambient temperature of 22° C. under the different atmospheres: air, air+1 ZR-200, nitrogen and nitrogen+1 ZR-200, for five days before irradiation. The residual oxygen content in the aluminium overwraps was controlled with a Servomex oxygen analyser before irradiation.

Gamma radiation was performed by using a Cobalt-60 isotope with a dose rate of 0.1 Mrad/hr. The irradiation dose was 35 kGy.

EXAMPLE 1.1

Visual Inspection

The irradiated saddles were visually inspected directly after irradiation. The degree of visual discolouration of the polypropylene/Kraton material and the visual damage of the rubber injection-port were evaluated. As a reference sample a non-irradiated polypropylene/Kraton saddle was studied. The properties of polymeric materials are affected by radiation as a result of the chemical changes in the polymer molecules. In the visual inspection directly after irradiation in air the PP/Kraton material has become yellow and the rubber injection-port has been damaged. When using an absorber, ZR-200, this colour change of the material does not occur and no visual damage of the rubber injection-port has been seen.

EXAMPLE 1.2

UV-Absorption

The ultraviolet absorption of the polypropylene/Kraton mixture, irradiated and non-irradiated, was analysed with a Shimadzu Spectrophotometer UV-265. A rectangular shaped (8 * 40 mm) polypropylene/Kraton sample piece with a thickness of 1 mm was used. The absorption of UV-light was measured in different atmospheres and then subtracted with the absorption from the non-irradiated material. As can be seen in Table 1, there is a pronounced effect on the UV absorption of the PP/Kraton material after γ-irradiation in the presence of an oxygen absorber. This indicates that the primary and secondary events taking place in the material are suppressed by the exclusion/consumption of oxygen. Table 1 one shows UV light absorption of polypropylene/Kraton samples irradiated in different atmospheres at 35 kGy gamma radiation subtracted with the absorption from the non-irradiated sample.

TABLE 1

| Sample | Absorbance at 282 nm |
| --- | --- |
| Air | 1.0 |
| Air + ZR-200 | 0.26 |
| Nitrogen | 0.34 |
| Nitrogen + ZR-200 | 0.16 |

EXAMPLE 1.3

IR-Absorption

The aforedescribed samples of polypropylene/Kraton material was examined before and after irradiation by IR-spectroscopy. A Perkin-Elmer 1600 FTIR Spectrophotometer was used to identify the change in structure on the surface (2 μm deep), in the infrared region (4000–625 cm$^{-1}$).

The use of an external oxygen scavenger prior to and during exposure to high-energy irradiation operate by suppressing the formation of hydroperoxides during the free-radical oxidative chain process which immediately follows exposure to high-energy irradiation. The post-γ-oxidation as is evident by FTIR spectra, i.e. a gradual increase in absorbencies at approximately 3400 $cm^{-1}$, 1720 $cm^{-1}$, and 1200 $cm^{-1}$ during subsequent storage of polypropylene (1) has not been observed in this work. In Table 2, data for samples immediately after irradiation is presented, and as can be seen peaks corresponding to carbonyl (1750 $cm^{-1}$), double bonds (1650 $cm^{-1}$) and carbon-oxygen bonds (1150 $cm^{-1}$) there is a significant reduction in samples irradiated with an oxygen absorber.

Table 2 shows FTIR peak height indexes of polypropylene/Kraton samples, non-irradiated and irradiated in different atmospheres with a dose of 35 kGy gamma-radiation. The peak heights at 1750, 1650 and 1150 $cm^{-1}$ are all compared with the peak height at 1460 $cm^{-1}$.

TABLE 2

| Sample | Peak height index at 1750 $cm^{-1}$ | Peak height index at 1650 $cm^{-1}$ | Peak height index at 1150 $cm^{-1}$ |
| --- | --- | --- | --- |
| Non-irradiated | 0.31 | 0.17 | 0.27 |
| Air | 0.12 | 0.22 | 0.12 |
| Air + ZR | 0.14 | — | 0.20 |
| Nitrogen | 0.18 | — | 0.12 |
| Nitrogen + ZR | 0.06 | 0.10 | 0.14 |

EXAMPLE 1.4

Tensile Strength and Elongation Break

From the kinetic theory of rubber elasticity one gets the expression $E=\delta s/\delta e=3\rho RT/M_c$ which indicates that the modulus of a rubber should increase linearly with increasing temperature. This effect can be shown by irradiation of a material not normally considered as a rubber, such as high-density polyethylene, and then observing the modulus behaviour in the region above the melting point of the unirradiated material. The effect of the radiation is to produce cross-links, as well as to reduce crystallinity, and when the crosslink density gets sufficiently high the chains are linked into a flexible three-dimensional network and the material shows rubber like behaviour above its melting temperature. Radiation also has an effect on the mechanical properties of the polyethylene below the melting temperature, and these changes are largely a result of loss of crystallinity owing to the irradiation. This is shown, for example, by the drop in modulus in the room-temperature region and below. Evidently at the very high dosages the additional stiffening effect of an increasing degree of cross-linking between chains more than counter balances the increased flexibility due to loss of crystallinity. Mechanical data for non-irradiated and irradiated PP/Kraton materials direct after irradiation are presented in Table 3.

Table 3 shows tensile strength and elongation at break of the aforedescribed samples. The Tensile-Strain testing before and after irradiation was carried out at 25° C. using rectangular shaped test pieces (10 * 55 mm) with a thickness of 1 mm. An Universal Testing Machine, Model Alwetron TCT5, was used at a crosshead speed of 500 mm/min.

TABLE 3

| Sample | F [N] | Elongation at break, ε [%] |
| --- | --- | --- |
| Non-irradiated | 217 ± 13 | 855 ± 48 |
| Air | 201 ± 9 | 930 ± 128 |
| Air + ZR | 205 ± 7 | 911 ± 129 |
| Nitrogen | ± | ± |
| Nitrogen + ZR | 193 ± 6 | 800 ± 155 |

The data indicates that the interpenetrating network between PP and Kraton undergoes minimal changes in tensile strength and elongation at break upon irradiation in the presence of an oxygen absorber. However, irradiated materials in the presence of air does not show significant degradation and/or crosslinking. This might be due to the counter balance of two effects. For aliphatic polymers, the rubbery polymers are most radiation resistant, presumably because many scissions must occur to reduce significantly the integrity of the article. In highly crystalline polymers, only a relatively small number of scissions in the intercrystalline tie molecules is required to affect drastically the toughness of the material. Because changes in the tensile properties of polymers result from radiation-induced chain scission or crosslink formation, it may be possible to devise copolymers or blends of polymers where these two effects compensate. Attempts at demonstrating this approach have been only partially successful with methyl methacrylate (PMMA undergoes chain scission upon irradiation) copolymerized with styrene-butadiene rubbers (SBR, crosslinks upon irradiation). After storage one might expect a more significant difference between the samples in Table 3.

EXAMPLE 1.5

Chemiluminiscence

Chemiluminiscence is a method to measure photons emitted during the decay of hydroperoxides. Fast Chemiluminiscence analysis was studied with a commercial Thermo Luminescence Dosimeter (TLD) from Alnor Instruments AB. With the TLD the number of photons emitted from irradiated and non-irradiated Polypropylene/Kraton samples was determined. The Chemiluminiscence analysis was performed under nitrogen atmosphere at 100° C. or 130° C. for 70 s.

Table 4 shows chemiluminiscence at 100° C. and Table 5 at 130° C.

TABLE 4

| Sample | Number of photons |
| --- | --- |
| Non-irradiated | $1.6 * 10^4$ |
| Air | $3.5 * 10^4$ |
| Air + ZR | $1.7 * 10^4$ |
| Nitrogen | $3.1 * 10^4$ |
| Nitrogen + ZR | $1.8 * 10^4$ |

TABLE 5

| Non-irradiated sample | Number of photons |
| --- | --- |
| Stored without ZR | $1.8 * 10^4$ |
| Stored with ZR | $1.4 * 10^4$ |

As can be seen in Table 4, there is a decrease in photons from the materials irradiated in the presence of an oxygen absorber and as demonstrated in Table 5, also in a non-irradiated sample.

EXAMPLE 1.6

Thermogravimetric Analysis (TG)

With a Thermogravimetric Analysing System, Mettler TA 3000, consisting of a microbalance Mettler MT5 and a furnace controlled by a TC 10 A processor, the loss of mass of the polypropylene/Kraton material was measured as a function of time. Ca 35 mg sample was heated from room temperature to 600° C. with a heating speed of 5° C./min. Irradiated and non-irradiated samples were analysed.

TABLE 6

| Sample | Onset [°C.] | Slope [mg/K] |
| --- | --- | --- |
| Non-irradiated | 407.3 | −1.09 |
| Air | 405.4 | −0.87 |
| Air + ZR | 403.4 | −0.74 |
| Nitrogen + ZR | 407.5 | −0.88 |

The results from the TG analysis, shown as onset temperature and degradation temperature slope, show no significant difference between the samples.

EXAMPLE 1.7

Differential Scanning Calorimetry (DSC)

A Mettler TA 3000 system was used with a Differential Scanning Calorimetry measuring cell DSC 30 and a processor TC 10A. Ca 20 mg samples were heated from −100° C. to 300° C. at a heating rate of 10° C./min under nitrogen atmosphere. Irradiated and non-irradiated samples were analysed.

TABLE 7

| Sample | Melting peak [°C.] | Δ H [J/g] |
| --- | --- | --- |
| Non-irradiated | 127.6 | 16.3 |
| Air | 137.4 | 15.0 |
| Air + ZR | 127.4 | 16.3 |
| Nitrogen + ZR | 129.0 | 19.2 |

The results from the DSC analysis, melting peak and ΔH of the PP part of the saddle material, are shown in Table 7. A non-irradiated saddle and irradiated saddles in different atmospheres, which can be seen in table 7, are analysed. As can be seen in table 7, the saddle material irradiated in air shows an increase in melting point and a decrease in ΔH of the PP material, compared to the non-irradiated material and the material irradiated with an oxygen absorber added. The increase in melting temperature, compared to the non-irradiated sample, of the PP is due to crosslinking and decrease in ΔH, compared to the non-irradiated sample, indicates a reduction in crystallinity of the material due to the formation of crosslinking when irradiated air.

EXAMPLE 2

Gas Chromatography Mass-Spectrometry (GC-MS)

In order to identify the main volatile products formed by gamma irradiation of Excel saddles in different atmospheres, samples were analysed by head space GC-MS. The analysis apparatus consisted of a GC model Hewlett Packard 5890 equipped with a mass detector 5972 and a head space sampler 7694. The samples were heated at 130° C. for 60 minutes before transferred to the GC apparatus. As column in the GC separation a HP Ultra 2,50 m * 0.32 mm was used. The temperature programme used was the following; 60° C. for 10 min, 10° C./min up to 230° C., injection temperature: 220° C.

TABLE 8

Head space GC-MS of irradiated Excel saddles, 35 kGy, gamma

| Compound | non-irrad. area [%] | air area [%] | air + abs area [%] |
| --- | --- | --- | --- |
| Cyclohexene |  | 5.6 |  |
| 2-Propoxyethanol | 5 | 62,9 | 64,9 |
| Cyclohexanol |  | 2 |  |
| Cyclohexanon |  | 6,1 |  |
| Unknown | 70 | 3,4 | 3,4 |

The results from the Head space GC-MS analysis are shown in Table 8 above. The number of volatile degradation compounds are decreasing when the PP/Kraton material is irradiated in the presence of an oxygen absorber compared to when the material is irradiated in the presence of air.

The unknown compound that exists as degradation compound is probably from an aromatic antioxidant of the PP material. The material irradiated in the presence of an oxygen absorber has the same degradation compounds as the non-irradiated sample which is of major importance.

The test demonstrates how potentially toxic degradation products like cyclohexene, cyclohexanol and cydohexanon are absent in the samples which have been irradiated in the presence of an oxygen absorber.

We claim:

1. A process for sterilizing an article made from a polymeric material by means of radiation, comprising:
   a) enclosing the said polymeric material in a gas impermeable package together with an oxygen absorber having access to a supply of water,
   b) storing the package for at least 48 hours to allow consumption of substantially all the oxygen in the package and the oxygen dissolved in the polymeric material, and
   c) thereafter subjecting the package and its content to a sterilising dosage of γ-radiation.

2. A process in accordance with claim 1 wherein the polymeric material is stored for from 48 hours to several weeks, with the oxygen absorber.

3. A process in accordance with claim 1 wherein the polymeric material includes at least one polymer belonging to the category that can be secondarily oxidized and cross-linked.

4. A process in accordance with claim 1 wherein the polymeric material includes polypropylene and/or polyethylene.

5. A process in accordance with claim 1 wherein the gas impermeable package comprises an aluminium foil.

6. A process according to claim 1 wherein the gas impermeable package is sealed in air.

7. A process according to claim 1 wherein the oxygen absorber is iron-based and contain crystalline water.

8. A process in accordance with claim 1 wherein an article for medical use is sterilized.

9. A process in accordance with claim 1 wherein the article made from a polymeric material is a container containing a γ-radiation sterilizable product.

10. A process according to claim 9 wherein the product is a parenterally administerable preparation.

11. A γ-radiation sterilized medical article made of a polymeric material produced by:
   a) enclosing the medical article in a gas impermeable package together with an oxygen absorber and a supply of water;
   b) sealing the package and storing it for at least 48 hours to consume substantially all the oxygen dissolved in the matrix of the polymeric material; and then
   c) subjecting the package and its content to a sterilizing dosage of γ-radiation.

12. A γ-radiation sterilized container made of a polymeric material, and containing a radiation sterilizable medical product intended for parenteral administration, produced by:
   a) aseptically filling and sealing the container with the medical product,
   b) enclosing the medical container in a gas impermeable package together with an oxygen absorber and a supply of water;
   c) sealing the package and storing it for at least 48 hours to consume substantially all the oxygen dissolved in the matrix of the polymeric material;
   d) subjecting the package and its content to a sterilizing dosage of γ-radiation.

13. A container produced according to claim 12 characterized in that said container contains amino acids and/or a lipid emulsion.

14. A container produced according to claim 12 wherein said step a) is conducted in an oxygen depleted atmosphere.

15. A container produced according to claim 12 wherein said step b) is conducted in an oxygen depleted atmosphere.

* * * * *